United States Patent
Perchik et al.

(10) Patent No.: US 7,947,019 B2
(45) Date of Patent: May 24, 2011

(54) CATHETER RETENTION ASSEMBLY AND METHOD OF USE

(75) Inventors: Joel E. Perchik, Jackson, TN (US); Theodore J. Beyer, Queensbury, NY (US); William M. Appling, Granville, NY (US)

(73) Assignee: Angio Dynamics, Inc, Latham, NY (US)

( * ) Notice: Subject to any disclaimer, the term of this patent is extended or adjusted under 35 U.S.C. 154(b) by 0 days.

(21) Appl. No.: 11/506,505

(22) Filed: Aug. 18, 2006

(65) Prior Publication Data

US 2008/0045894 A1 Feb. 21, 2008

(51) Int. Cl.
*A61M 5/32* (2006.01)
*A61M 3/00* (2006.01)
*A61M 25/00* (2006.01)

(52) U.S. Cl. .......................... 604/175; 604/43; 604/523
(58) Field of Classification Search .................. 604/29, 604/164.01, 164.03, 164.04, 164.05, 164.07, 604/164.1, 165.01, 165.02, 165.03, 174, 604/175, 177, 178, 43, 523
See application file for complete search history.

(56) References Cited

U.S. PATENT DOCUMENTS

| | | | | |
|---|---|---|---|---|
| 3,726,279 A * | 4/1973 | Barefoot et al. | | 606/151 |
| 4,266,999 A * | 5/1981 | Baier | | 156/227 |
| 4,278,092 A * | 7/1981 | Borsanyi et al. | | 604/175 |
| 4,676,782 A * | 6/1987 | Yamamoto et al. | | 604/175 |
| 4,772,268 A | 9/1988 | Bates | | |
| 5,292,311 A * | 3/1994 | Cope | | 604/165.02 |
| 5,830,184 A * | 11/1998 | Basta | | 604/104 |
| 6,156,016 A * | 12/2000 | Maginot | | 604/264 |
| 6,231,547 B1 | 5/2001 | O'Hara et al. | | |
| 6,293,927 B1 * | 9/2001 | McGuckin, Jr. | | 604/266 |
| 6,695,832 B2 * | 2/2004 | Schon et al. | | 604/544 |
| 6,796,991 B2 * | 9/2004 | Nardeo | | 606/191 |
| 6,939,328 B2 * | 9/2005 | Raulerson | | 604/175 |
| 7,104,982 B2 * | 9/2006 | McDaniel | | 604/533 |
| 2004/0186461 A1 | 9/2004 | DiMatteo | | |
| 2004/0236314 A1 * | 11/2004 | Saab | | 604/539 |
| 2005/0209581 A1 | 9/2005 | Butts et al. | | |
| 2005/0209583 A1 * | 9/2005 | Powers et al. | | 604/533 |
| 2006/0129134 A1 | 6/2006 | Kerr | | |
| 2006/0200111 A1 * | 9/2006 | Moehle et al. | | 604/539 |

* cited by examiner

*Primary Examiner* — Theodore J Stigell
*Assistant Examiner* — William Carpenter
(74) *Attorney, Agent, or Firm* — Tara L. Custer

(57) ABSTRACT

A catheter retention assembly and method of use with a catheter. The assembly has a carrier system and a cuff positioning device with an in-growth cuff and a lumen having an inner wall adapted to be mounted on the outer surface of the catheter, and a carrier system with an inner surface and an outer surface in contact with the inner wall of the cuff positioning device. The carrier system holds the lumen in a first radial state. When the carrier system is removed, the lumen contracts to a second radial state, and the inner wall of the cuff positioning device provides sufficient surface adherence to the outer surface of the catheter, so as to maintain the position of the cuff positioning device relative to the catheter, and to allow for catheter exchange.

18 Claims, 7 Drawing Sheets

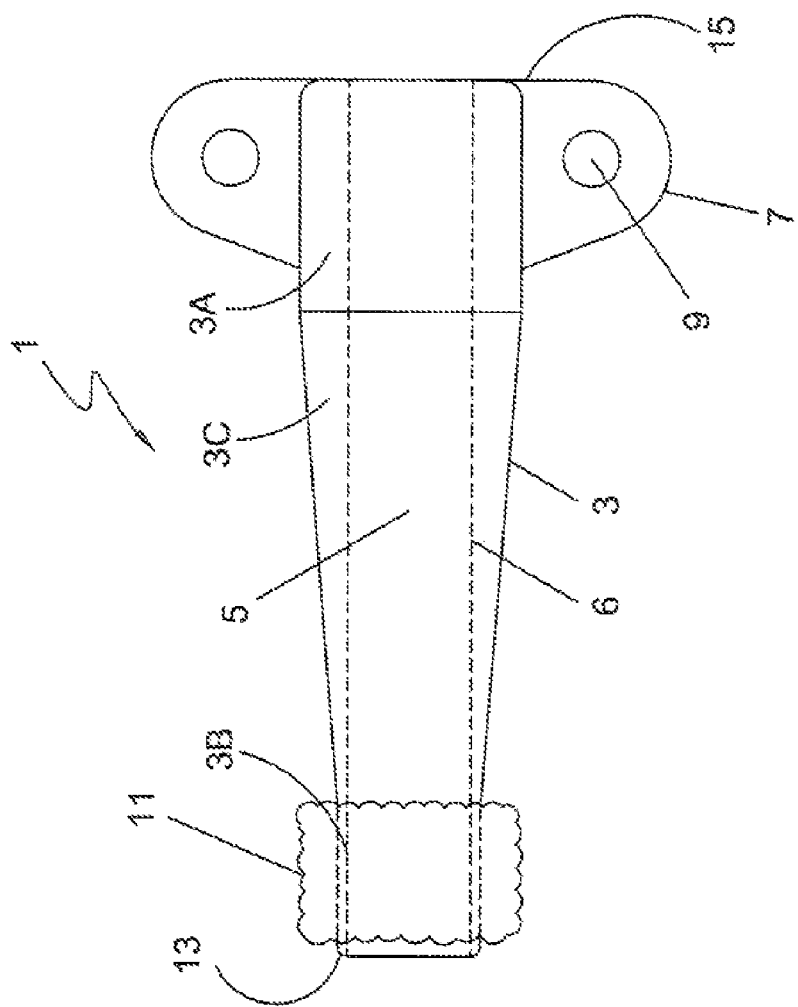
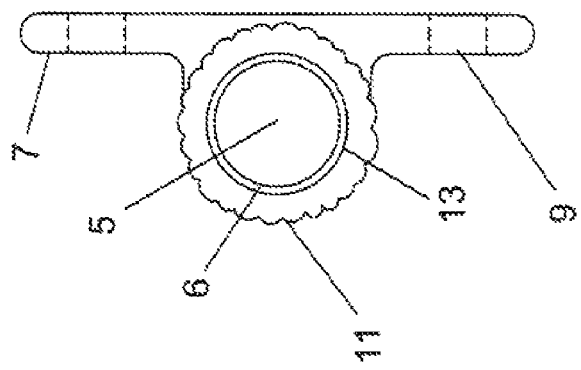
FIG. 3A
FIG. 3B

CATHETER RETENTION ASSEMBLY AND METHOD OF USE

CROSS-REFERENCE TO RELATED APPLICATIONS

Not Applicable

STATEMENT REGARDING FEDERALLY SPONSORED RESEARCH

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to the field of vascular access devices, and more particularly, to devices and methods for positioning and retaining long-term vascular access catheters.

2. Description of the Related Art Including Information Disclosed Under 37 CFR 1.97 and 1.98

Vascular access catheters provide venous access to the central circulatory system of a patient. Vascular access catheters placed for a short time period, typically less than two weeks, are called acute catheters. For those medical conditions requiring long term access to the circulatory system, chronic or permanent vascular access catheters are used. These catheters are designed to remain within the patient for indefinite periods, often more than a year. Permanent or chronic venous access catheters are usually placed through a subcutaneous tunnel and include central venous catheters, dialysis catheters, peritoneal catheters, and peripherally inserted central catheters, also known as PICC lines.

The long-term catheter is typically used for the delivery of intravenous fluids, medications such as chemotherapy drugs and antibiotics, and blood products. Venous access catheters may also be used as access mechanisms for blood sampling and the administration of contrast agents during diagnostic Computer Tomography (CT) procedures. Dialysis catheters are used to access the venous system during hemodialysis, a medical procedure used to cleanse the blood of patients whose kidneys do not function properly.

Vascular access catheters are placed within the central circulatory system such that the catheter tip is exposed to high rate blood flow, typically in the right atrium. This allows rapid delivery and dilution of drugs into the bloodstream, and thus, more effective treatment. In the case of dialysis catheters, high flow rates provide faster and more effective blood cleansing. Optimal location of the catheter tip in a large blood vessel is also necessary in order to decrease the rate of catheter occlusion.

Another clinical requirement of vascular access catheters is that the catheter be placed so as to eliminate any dislodgement or movement of the catheter during long-term use. Catheter movement may result in sub-optimal treatment due to catheter tip misalignment Movement may also result in catheter leakage, infection and blood loss. Dislodgement of a vascular access catheter may even result in death, due to extensive blood loss from the jugular or other large vein.

To fix and retain the position of a long-term catheter in a patient's body, the catheter is typically inserted by tunneling the catheter through a subcutaneous tissue track. This tunneling technique may decrease infection rates at the site of cutaneous insertion, which is the primary site of entry for microorganisms on a catheter. Studies have shown that compared to standard catheter placement, tunneling decreases bacteria colonization.

To create a subcutaneous tunnel, a first incision is made in the patient's skin approximately several inches away from where the catheter will enter the target vein. A second incision is made at the location where the catheter will enter the vein. A tunnel track is created through the fascial tissue between the two incisions. The distal end of the catheter is then inserted into the first incision and advanced through the tunnel track where it emerges from the skin at the second incision, or exit site. The distal portion of the catheter is then inserted into the target vein.

Dialysis catheters are typically tunneled through the chest wall tissue, entering the internal jugular vein at the neck area. They may also be placed in the subdlavian vein just below the collar bone. Peritoneal catheters are tunneled from the peritoneum to the exit site of the catheter, near the navel. As with standard dialysis catheters, the main consideration with peritoneal catheters is the potential for infection at the exit site or peritonitis.

PICC lines, smaller in diameter, are typically introduced through the basilic or cephalic vein into the central circulatory system. Although traditionally PICC lines have been inserted directly into the target vein, placing PICC lines through a subcutaneous tunnel is an emerging trend. For these lines, the tunnel is usually created in the lower or upper arm region, with the catheter entering the target vein near the shoulder. Central venous catheters are larger in diameter than PICC lines and are typically placed when no peripheral veins are available, when medications cannot be introduced into a peripheral vein without vessel damage, or when central venous pressure monitoring is required. Tunneling of a central venous catheter is similar to the technique used for dialysis catheters.

Tunneled catheters may include a circular in-growth cuff attached to the outer surface of the catheter shaft near a bifurcation hub. The in-growth cuff is made of a porous or fibrous material which promotes tissue in-growth by allowing the tunnel track tissue to grow into the in-growth cuff material. The in-growth cuff thus acts as an anchor to help secure the catheter in place and prevent movement of the catheter. The in-growth cuff also helps to provide protection against infections related to vascular access catheters by sealing the tunnel track. The in-growth cuff prevents undesired movement and inadvertent removal of the catheter and thereby prevents excessive blood loss or death. Because it takes approximately two weeks for tissue to become fully incorporated into the in-growth cuff, the physician typically fixes the catheter to the patient's skin immediately after insertion. The catheter may be securely fixed to the patient's skin by sutures stitched through suture wings on the hub. Alternatively, an adhesive bandage or other skin attachment mechanism may be used.

To optimize treatment results, the distal tip of the catheter must be precisely placed in a large blood vessel such as the right atrium, and the in-growth cuff must be positioned and fixed inside of the patient's body. Positioning the catheter within the right atrium provides the high blood flow rates required for efficient dialysis, or in the case of PICCs, rapid delivery and dilution of drugs into the bloodstream, and thus more effective treatment. Optimal location of the catheter tip in a large blood vessel is also necessary in order to decrease the rate of catheter occlusion. Optimal placement of the catheter tip will make the catheter tip less likely to contact or rest up against the inside of a blood vessel wall, thereby blocking catheter ports, or causing damage to the vessel wall from the catheter.

Optimal catheter cuff placement is critical for secure fixation of the catheter over long periods of time. It is generally accepted that the ideal cuff placement is at a depth of at least 2 cm to approximately 3.5 cm from the incision entry site. This position provides for optimal in-growth of the cuff and secure fixation. Proper catheter cuff placement also ensures a tight seal between the catheter and the tunnel track, thereby reducing risk of infection, and associated complications. Cuffs placed too close to the incision site will result in sub-optimal fixation and the increased risk of peri-catheter leakage and infection. If the physician is forced to place the cuff deeper into the tunnel track than desired in order to achieve optimal catheter tip placement, catheter removal or exchange becomes problematic as it is difficult to remove a cuff that is too deeply tunneled. Studies have also shown that deep tunneling may lead to increased risk of catheter infection.

Patient comfort is directly related to the position of the cuff because cuff position determines where the catheter will be sutured to the patient's body. Most venous access catheters include a suture wing component attached directly to the bifurcation hub. Suturing the catheter in a less than optimal location on the patient's body may not only lead to discomfort but may also increase the risk of catheter movement or dislodgement. For example, if a catheter is sutured to a female's chest, the natural movement of the breast may compromise catheter fixation.

If optimal cuff placement cannot be achieved, the physician may not be able to utilize the suture wings for securement to the patient's skin. Instead, the physician may be forced to suture the catheter to the skin surface at a location distant from the suture wings. To do this, the physician will wrap the suture directly around the catheter shaft at the desired location. Although this method may achieve temporary fixation of the catheter until cuff in-growth occurs, it may compromise the catheter's lumen due to compression by the suture line. Reduced lumen diameter will result in reduced flow rates through the catheter, which in turn, will compromise treatment.

In summary, the difficulty associated with placement of the catheter tip and the catheter cuff is that the catheter tip and the cuff are fixed relative to each other. Thus, optimum positioning of one is likely to result in less than optimal positioning of the other, resulting in problems associated with treatment efficiency, catheter fixation, infection risk, patient comfort and comprised flow rates, as described above. Thus, there exists a need in the art to be able to independently position the tip and cuff during a tunneled catheter placement to ensure optimal positioning of all elements of the catheter.

Several different types of catheters have been developed in an attempt to address the need for precise positioning and maintenance of the catheter tip and cuff during catheter placement. For example, manufacturers of some vascular access catheters offer catheters of varying lengths to accommodate different patient anatomy and placement preferences. The catheter length requirement for catheter tip placement at the junction of the superior vena cava and right atrium is typically estimated by measuring the distance of the path from the tunneled insertion site to the right atrium. The appropriate length catheter is then selected by the physician. Commercially available catheter lengths often only approximate the ideal length, requiring the physician to adjust placement of the catheter, which may result in sub-optimal positioning. In addition, even if the overall length of a catheter is available, the desired distance between the cuff and tip varies by patient anatomy. To address this problem, physicians may customize the catheter by trimming the distal end of the catheter prior to placement Distal trimming is disadvantageous for several reasons. Trimming requires additional physician time to accurately measure and trim the catheter. Trimming the catheter may increase the chance of error in achieving the proper length and overall placement of the catheter. Trimming the end of the catheter can result in unwanted sharp edges, and the modified distal tip may hinder catheter advancement through the tunnel and into the vascular system. Trimming can also weaken the integrity of the catheter, thus compromising treatment efficiency or increasing the risk of shaft breakage. Additionally, some vascular access catheters have distal tips that are tapered or otherwise uniquely shaped and accordingly cannot be trimmed at all.

Several different types of catheters have been proposed to address the need for accurate catheter placement by first placing the catheter within the central venous system and then trimming the proximal end of the catheter shaft. The distal tip of the catheter is first placed in the desired location and then the proximal portion of the shaft extending outside of the patient's body is trimmed, after which a bifurcation or other hub configuration is attached to the proximal shaft end by the physician. Trimming the catheter proximally exposes less of the catheter to potential damage and ensures precise positioning of both the proximal and distal ends of the catheter, but there are key disadvantages to this technique. Typically, the cuff is permanently pre-attached to the catheter shaft and therefore cannot be adjusted independently of the catheter tip. This technique is also disadvantageous in that it requires the physician to perform additional steps to attach the hub after initial catheter placement, thereby increasing procedure time. Mechanically attaching a hub to a catheter shaft also increases the potential for leakage at the hub connection and presents concerns about the long-term structural integrity of the attached components.

Another type of commercially available device facilitates precise positioning of both the distal and proximal ends of the catheter by use of an attachable suture wing connector that may be mounted separately onto the catheter shaft This design provides for adjustable positioning of the suture wing, but does not provide for independent customization of the cuff position. In addition, the suture wing is not permanently affixed to the catheter shaft and thus may be inadvertently moved or even removed, resulting in the problems associated with sub-optimal catheter fixation.

There has not been proposed a catheter assembly that addresses the need for optimally and permanently customizing the position of the catheter cuff and the catheter tip relative to one another in a patient body during catheter placement The present invention addresses this need by utilizing a catheter retention assembly comprised of a cuff positioning device with an in-growth cuff and a securing means. The device includes a carrier system which, when mounted on a vascular access catheter, is slidably and longitudinally moveable along the catheter shaft. Once the catheter retention assembly is positioned as desired relative to the distal tip of the catheter, the cuff positioning device may be permanently fixed to the catheter shaft, thus providing a means for customizing the cuff position relative to the tip position. Once the cuff positioning device is locked in place on the catheter shaft, the catheter will not move or slip in relation to the cuff positioning device. Since a securing means is also mounted on the cuff positioning device, the physician is able to temporarily fix the exposed catheter in the desired location on the patient's skin until in-growth of the cuff has been established.

The combined design features of the current invention are not presently available in conventional catheters with fixed-position sutures and cuff assemblies. Using the device of the current invention to independently optimize cuff and tip placement eliminates problems with prior art devices and methods, including the problems of sub-optimal treatment outcomes, increased infection risk, compromised catheter integrity, insecure fixation and patient discomfort The instant invention may be applied to all types of vascular access catheters, including, but not limited to, hemodialysis catheters, peritoneal catheters, PICC lines, central venous catheters, and tunneled catheters, as described.

Accordingly, it is a purpose of the present invention to provide a catheter retention assembly, which provides for optimal, simultaneous, and permanent positioning of the catheter tip and the catheter cuff relative to one another during catheter placement by positioning the catheter tip and fixing the position of the cuff positioning device around the catheter. This enhanced permanent optimal placement will improve treatment outcomes and help lower the risk of infection in a patient, thereby enhancing the catheter's antimicrobial properties and ensuring that the lumen of the catheter is not compromised.

A further purpose of this invention is to provide a catheter retention assembly that will help to ensure that adjustment of the cuff automatically positions the external fixation mechanism such as a suture wing in the desired place on the patient's skin away from sensitive areas to ensure patient comfort, while not compromising the integrity of the catheter.

A further purpose of this invention is to provide a catheter retention assembly and method of placement that minimizes procedural steps and provides the physician with a simple, easy to use method of adjusting the location of a cuff without additional catheter assembly or trimming steps.

A further purpose of this invention is to provide an expander sheath that may be mounted around the shaft of a catheter and may be inserted between the inner wall of the cuff positioning device and the outer wall of the catheter shaft in order to allow the catheter to be exchanged with a new catheter, without removing the cuff.

Various other objectives and advantages of the present invention will become apparent to those skilled in the art as more detailed description is set forth below. Without limiting the scope of the invention, a brief summary of some of the claimed embodiments of the invention is set forth below. Additional details of the summarized embodiments of the invention and/or additional embodiments of the invention may be found in the Detailed Description of the Invention.

BRIEF SUMMARY OF THE INVENTION

The present invention provides for a catheter retention assembly that may be used to fix and retain the position of a catheter tip and a catheter cuff, thereby providing enhanced optimal catheter placement.

The present invention is advantageous in view of current catheters because it provides simultaneous optimal permanent placement of a catheter tip and a moveable catheter cuff within a tunneled track that are independent of each other. The present invention is also advantageous because it eliminates problems presented by current catheters with sub-optimal cuff placement, which can result in increased tunnel track infections and catheter movement or dislodgement. The present invention also overcomes problems of current catheters that require suturing the catheter to the patient in an undesirable location of a patient's anatomy.

The present invention solves these problems by providing a catheter retention assembly for use with a catheter that has a through lumen adapted for coaxial arrangement on a catheter shaft. The catheter retention assembly has a cuff positioning device, an in-growth cuff on the cuff positioning device, and a carrier system with an inner surface that surrounds the shaft of the catheter and an outer surface that is in contact with the inner wall of the cuff positioning device. When the carrier system is removed or activated, a sufficient surface adherence is created between the inner wall of the cuff positioning device and the outer surface of the catheter, so as to maintain the position-of the cuff positioning device relative to the catheter. The sufficient surface adherence between the inner wall of the cuff positioning device and the catheter is due to an interference fit relationship.

In one embodiment of the present invention, an in-growth cuff is mounted near the distal end of the cuff positioning device, and suture wings are mounted to the proximal end of the cuff positioning device. The cuff positioning device is mounted onto a carrier system which is mounted onto the catheter. The inner surface of the carrier system provides relatively low surface adherence to the outer surface of the catheter so as to permit the carrier system to be readily longitudinally moved along the catheter shaft for precise positioning. The carrier system holds the inner wall of the cuff positioning device in a first expanded radial state.

In another embodiment of the invention, the carrier system may be removed from the lumen of the cuff positioning device. The inner wall of the cuff positioning device then contracts to a second radial state. The carrier system may be removed from the lumen of the cuff positioning device by manually pulling in opposite directions abutting finger tabs that are intersected by at least one longitudinal splittable line at a carrier system hub and retracting the carrier system. Once the carrier system is removed, the position of the cuff positioning device relative to the catheter is maintained due to a sufficient surface adherence between the inner wall of the cuff positioning device and the outer surface of the catheter. The catheter tip and the in-growth cuff that is mounted on the cuff positioning device are thereby adjustable in relation to each other for precise positioning and are subsequently permanently fixed in relation to each other at the desired position relative to the patient's anatomy.

In another embodiment of the invention, a coiled spring may be embedded inside the wall of the cuff positioning device to provide an additional radially compressive force around the lumen of the cuff positioning device. This design further enhances the surface adherence between the inner wall of the cuff positioning device and the catheter, so as to further ensure that the cuff positioning device is retained in relation to the catheter.

In yet another embodiment of the invention, the cuff positioning device also has a means to secure the cuff positioning device to a patient's skin.

In another aspect of the invention, a method of retaining the position of a catheter using a catheter retention assembly that is pre-assembled on the catheter is disclosed. The method involves inserting a catheter having a cuff positioning device with an in-growth cuff and a lumen defined by an inner wall, and a carrier system, into a skin incision site. The method further involves positioning the distal end of the catheter at a desired location, moving the catheter retention assembly to a desired location, and removing the carrier system from the lumen of the cuff positioning device, so as to simultaneously fix the position of the catheter and the in-growth cuff on the cuff positioning device relative to one another. The carrier system may be removed by pulling abutting finger tabs in opposite directions away from the cuff positioning device and retracting the carrier system. After the carrier system is removed, the inner wall of the cuff positioning device contracts to a second radial state, thereby locking the cuff positioning device around the catheter. This permanently fixes the position of the cuff positioning device and the catheter relative to one another. The cuff positioning device is resilient, thereby allowing it to expand and contract.

In another aspect of the invention, a method of exchanging a catheter with a cuff positioning device for a new catheter is presented. This method involves mounting an expander over a catheter, advancing the expander between an inner wall of a cuff positioning device lumen and the outer wall of the catheter, expanding the lumen of the cuff positioning device, removing the catheter from the cuff positioning device, placing a new catheter through the expander, and removing the expander.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

BRIEF DESCRIPTION OF THE SEVERAL VIEWS OF THE DRAWINGS

The accompanying drawings are included to provide an understanding of the invention and constitute a part of the specification.

FIGS. 3A and 3B are, respectively, an end view and a side elevation view of the cuff positioning device without the carrier system in accordance with the present invention.

FIG. 6A is a cross-sectional view of the coiled spring in accordance with the present invention.

FIG. 6B is a cross-sectional end view of the cuff positioning device with the coiled spring embedded within the cuff positioning device wall in accordance with the present invention.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention.

The present invention pertains to a catheter retention assembly for use with a catheter and a method of inserting, positioning, and retaining the position of a catheter inside the body of a patient using the catheter retention assembly. The catheter retention assembly is illustrated in FIGS. 1-7D.

Figure 1:
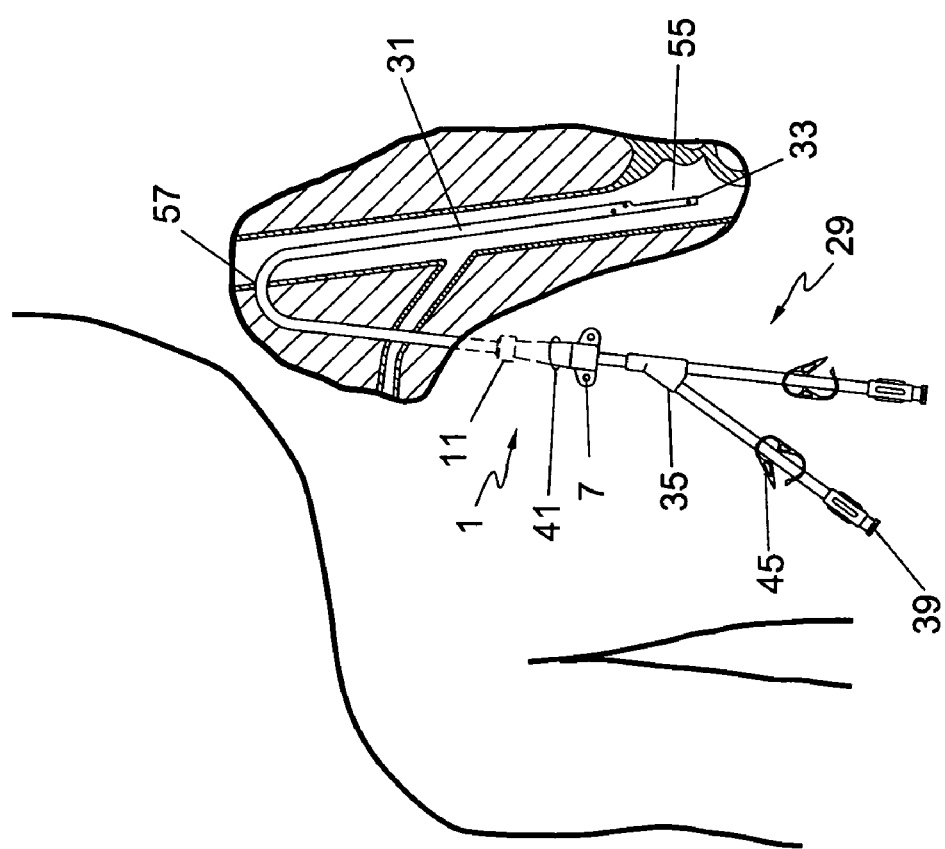
FIG. 1 is a schematic illustration of the cuff positioning device and catheter inserted into a patient with the distal tip of the catheter in the right atrium and the cuff positioning device inserted into the incision site.

FIG. 1 illustrates a preferred positioning of a tunneled venous access catheter 29. To obtain an optimal position, the distal end 33 of the venous access catheter 29 is inserted into a skin incision site 41 in a patient through a tunnel track into the jugular vein at veinotomy 57. The distal end 33 of the venous access catheter 29 is then advanced into the right atrium 55. The catheter shaft 31 is shown as it is extended into the right atrium 55. The cuff positioning device 1 is shown partially inserted into the tunnel track with the in-growth cuff 11 positioned at least 2 cm deep into the tunnel track. Optimal positioning of the in-growth cuff 11 allows the cuff positioning device 1 to be sutured to the patient's skin using the suture wings 7 at a location that minimizes patient discomfort and enhances fixation of the in-growth cuff 11.

Figure 2B:
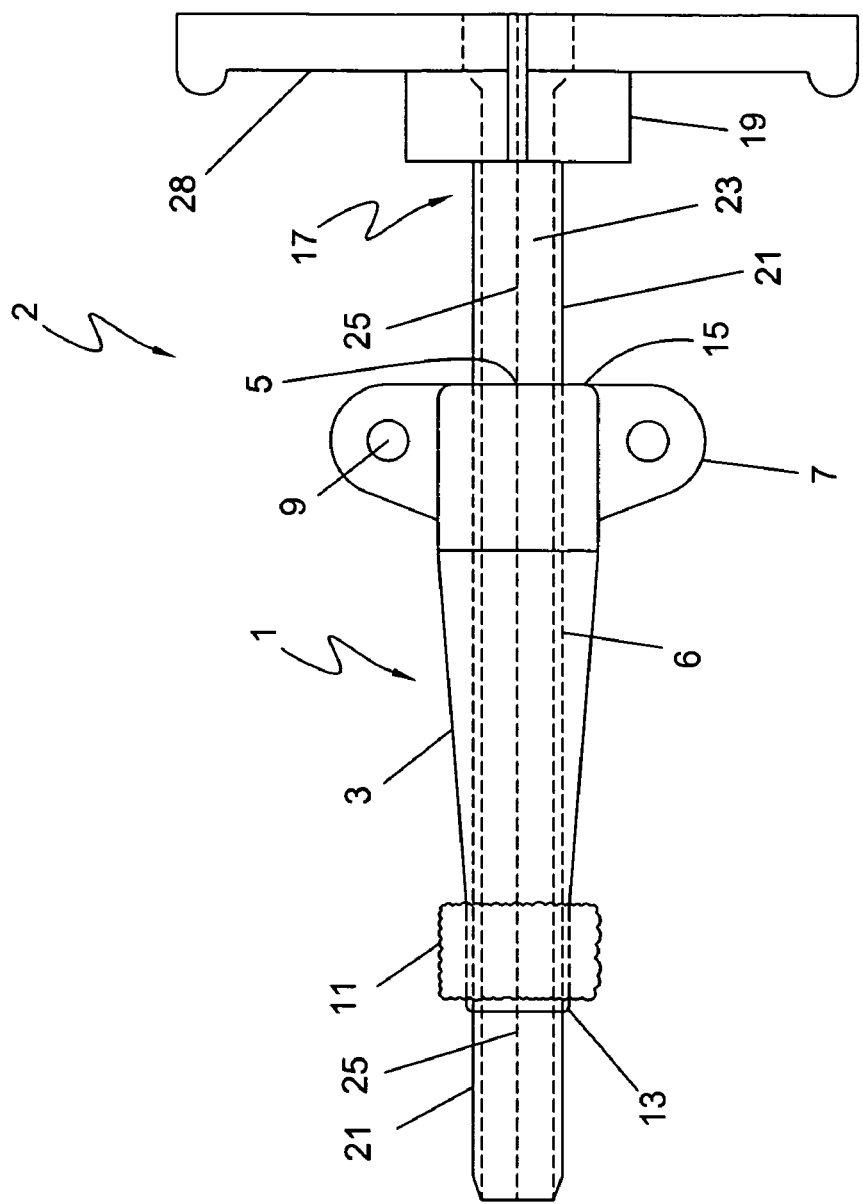
FIG. 2B is a longitudinal plan view of an embodiment of the device of this invention illustrating the catheter retention assembly. The catheter retention assembly has a cuff positioning device and a carrier system positioned through the cuff positioning device lumen.
Figure 2A:
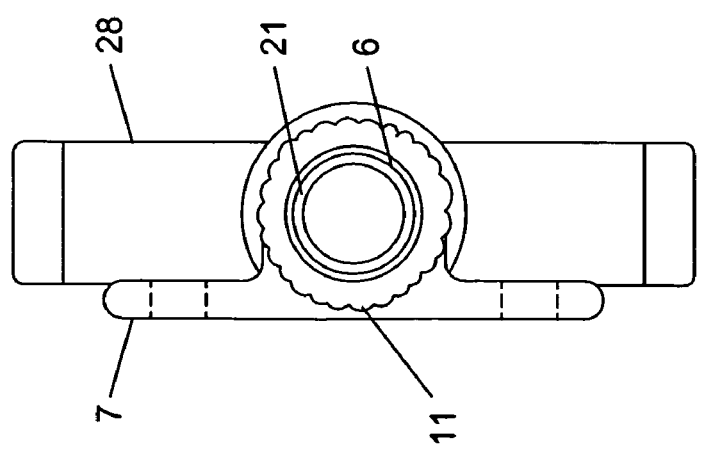
FIG. 2A is an end view of the catheter retention assembly.

In one embodiment of the invention, the catheter retention assembly 2 may be used to fix the position of a venous access catheter 29. FIGS. 2A and FIG. 2B illustrate the catheter retention assembly 2 prior to deployment on a venous access catheter 29. As shown in the longitudinal plan view of FIG. 2B, the catheter retention assembly 2 has a carrier system 17 that may be removed and a cuff positioning device 1. The carrier system 17 may have a carrier system hub 19 and a carrier system shaft 21 with a through lumen 23. The carrier system hub 19 has at least one carrier system finger tab 28 to facilitate longitudinal splitting of the carrier system 17. The cuff positioning device 1 is coaxially mounted on the carrier system shaft 21. The cuff positioning device 1 includes an in-growth cuff 11 that is mounted at or near the distal end 13 of the cuff positioning device 1, a cuff positioning body 3, and suture wings 7 located near the proximal end 15 of the cuff positioning device 1. Referencing FIG. 2A, the cuff positioning device 1 also includes a longitudinal cuff positioning device lumen defined by an inner wall 6, which extends from the distal end 13 of the cuff positioning device 1 to the proximal end 15 of the cuff positioning device 1, through which the carrier system shaft 21 is placed.

In one embodiment, the carrier system 17 has at least one splittable line 25 that facilitates manual longitudinal splitting and removal of the carrier system 17. The splittable line 25 runs longitudinally through the shaft 21 of the carrier system 17 and extends through a carrier system hub 19 at the proximal end of the carrier system 17. The splittable line 25 intersects abutting finger tabs 28 at the carrier system hub 19. The carrier system splittable line 25 may be pre-weakened or perforated in order to further facilitate removal and splitting of the carrier system 17 into even sections on either side of the splittable line 25. The distal end portion of the carrier shaft 21 may be tapered to facilitate advancement through the tunnel track.

As assembled, the carrier system 17 and cuff positioning device 1 is fixed in position relative to each other so as to prevent independent movement of either of these components. Fixation of the carrier system 17 and the cuff positioning device 1 are facilitated by an interference fit relationship between the cuff positioning device 1 and the carrier system 17. The interference fit relationship is due to the use of a combination of selected materials and dimensions of the components of the catheter retention assembly 2. Using a standard dialysis catheter carrier system as an example, the outer diameter of the carrier system 17 may be approximately 0.227 inches. The cuff positioning device 1 may have a diameter at the inner wall 6 of approximately 0.200 inches before expansion of 0.027 inches. These combined dimensions produce an interference fit relationship between the carrier system 17 and the cuff positioning device 1 when assembled, as shown in FIG. 2A.

The carrier system shaft 21 is preferably composed of a material such as polytetrafluoroethylene (PTFE). This material provides the carrier system shaft 21 with the necessary radial strength to prevent compression or collapse of the carrier system lumen 23 when the lumen 23 is compressed by the cuff positioning device 1, due to the interference fit relationship between the cuff positioning device 1 and the carrier system 17.

The cuff positioning device 1 is resilient and may be composed of an elastomeric material of a softer durometer and higher elastic limit than the carrier system shaft 21. The elastomeric material of the cuff positioning device 1 may be any suitable material. Preferably, the elastomeric material is any urethane-based material of a low durometer and high elastic limit. This permits the cuff positioning device lumen 5 (ref. FIG. 3A) to expand radially outward during assembly to accommodate the outer diameter of the shaft 21 of the carrier system 17. The high elastic limit of the material also ensures that the inner wall 6 of the cuff positioning device will return to its original unexpanded diameter after the carrier system 17 is removed.

Elastic limit is defined as the point at which a material no longer undergoes a change in strain linearly proportional to the change in stress. At stress levels below the elastic limit the material is elastic. Once the material exceeds this limit, it is undergoes plastic deformation, also known as permanent deformation. At this point the material will no longer return to its original size. The elastic limit of the elastomer used in the cuff positioning device 1 is sufficiently high to allow it to expand without undergoing plastic deformation, thereby returning to its original state after force is removed.

Figure 7A:
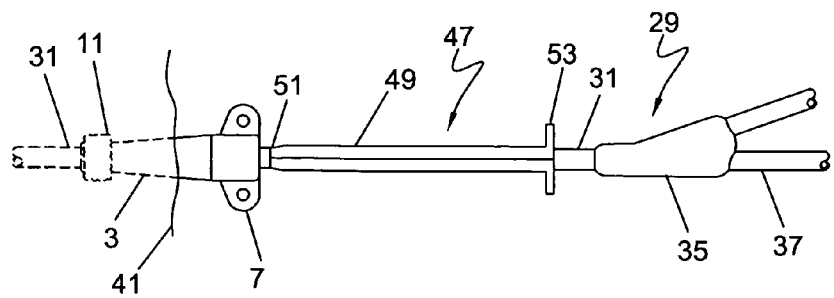
FIG. 7A is a partial view of a catheter with an expander sheath mounted around the catheter shaft, as it is being advanced toward the lumen of the cuff positioning device to facilitate catheter exchange.
Figure 7B:
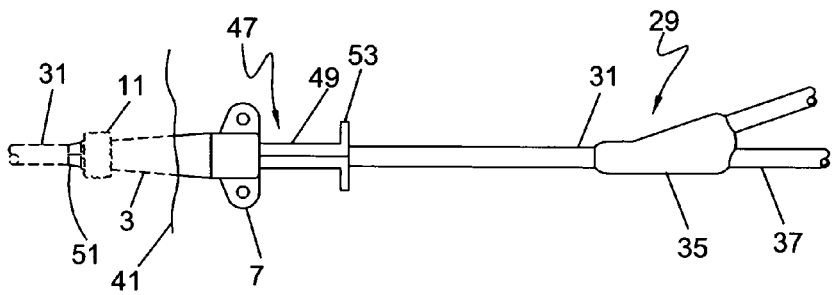
FIG. 7B is a partial view of a catheter with the expander sheath coaxially arranged around the catheter shaft as the catheter and the expander sheath are inserted into and advanced through the lumen of the cuff positioning device.

Although the carrier system 17 may have a longitudinally splittable configuration, other carrier systems are within the scope of this invention. For example, two independent semi-cylindrical tubular structures may be held in place within the cuff positioning device lumen 5 by the compressive force of the inner wall 6 of the cuff positioning device 1. An example of this embodiment is illustrated in FIG. 7B, as element 49 having finger tabs 53. Tubular materials may include PTFE, stainless steel, or other semi-rigid or rigid materials. A single semi-cylindrical tubular structure is also contemplated. In one such embodiment, the cylindrical tubular body has a single longitudinal slit extending the length of the tubular body. The slit is in a normally closed position, but may be expanded to an open position sufficient to allow removal from the cuff positioning device lumen 5 and catheter shaft 31.

The carrier system 17 may be any removable or non-removable carrier mechanism that is suitable for holding the inner wall 6 of the cuff positioning device 1 in a radially expanded state while the cuff positioning device 1 is advanced over the venous access catheter 29 and into the tunnel track of a patient. In the non-removable carrier design, the carrier system is retracted or activated, allowing the inner wall 6 of the cuff positioning device 1 to return to its second radially contracted state and to become fixed to the catheter shaft 31. A locking damp or spring, such as a C-shaped damp or spring or a helical clamp embedded in or attached directly to the cuff positioning device 1 may act as the carrier system 17. The carrier system 17 is activated to switch the cuff positioning device 1 from the first expanded radial state to a second contracted fixed position. Accordingly, the carrier system 17 may be, but is not limited to, a peel-away or non peel-away sleeve, a tube or cannula, or an internal mechanism within the body of the cuff positioning device 1.

Referring now to FIGS. 3A and 3B, the cuff positioning device 1 is illustrated as it is disassembled from the carrier system 17. FIG. 3A is an end view of the cuff positioning device 1 with the in-growth cuff 11. FIG. 3B illustrates a side elevation view of the cuff positioning device 1 of the invention with an in-growth cuff 11 near the distal end 13 of the cuff positioning device 1. The cuff positioning device 1 is preferably approximately 1.5 inches in length, but may also be of varying lengths to accommodate venous access catheters of different sizes and types. The cuff positioning device 1 has a cuff positioning wall 3 and a cuff positioning device lumen 5 defined by an inner wall 6. The wall has a first wall 3A thickness at the proximal end, a second, smaller wall 3B thickness at the distal end, and an intermediate wall 3C thickness between the proximal end and the distal end, wherein the intermediate wall thickness smoothly decreases from the proximal end 15 to the distal end 13. The cuff positioning device 1 is tapered from a first diameter at the proximal end 15 of the cuff positioning device 1 to a second smaller diameter at the distal end 13 of the cuff positioning device 1. The distal end 13 is configured for insertion into a patient's body, and the proximal end 15 is configured to remain outside of a patient's body, as illustrated in FIGS. 5B-5C and 7A-7D. The tapered design of the cuff positioning device 1 facilitates insertion and advancement of the venous access catheter 29 into the tunnel track during catheter placement. The tapered profile of the cuff positioning device 1 also minimizes inward migration of the cuff positioning device 1 within the tunnel track prior to tissue incorporation of the in-growth cuff 11. The tapered profile of the cuff positioning body 3 also provides a temporary tunnel sealing function by virtue of the expanded proximal outer diameter of the cuff positioning device 1.

The cuff positioning body 3 has an in-growth cuff 11 that is circumferentially mounted near the distal end 13 of the cuff positioning device 1. The in-growth cuff 11 promotes tissue in-growth, thereby permanently fixing the venous access catheter 29 in place and creating a barrier to the entrance of bacteria into the tunnel track from the skin surface. The in-growth cuff 11 may be approximately 0.16 inches in length. However, any length sufficient to promote tissue in-growth within the tunnel is within the scope of this invention. The in-growth cuff 11 may be made of any suitable porous or fibrous material. Preferably, the material is a polyester material, such as Dacron®. The in-growth cuff 11 may be embedded with medicinal agents that enhance tissue in-growth or minimize infection.

The cuff positioning body 3 also has a means to secure the ruff positioning device 1 to a patient's skin. Such means may be a pair of suture wings 7 disposed on the proximal end 15 of the cuff positioning device 1. The suture wings 7 may have a width of approximately 0.83 inches between the outer tips of the suture wings 7. The suture wings 7 have suture wing holes 9 located in the center of each suture wing 7. Each of the suture wing holes 9 may have a diameter that is approximately 0.090 inches. The suture wings 7 may be formed as part of the cuff positioning device 1 by using injection molding, or alternatively may be separately molded over the cuff positioning device 1. The suture wings 7 may be made of any suitable material. Preferably, the suture wings 7 are made of any urethane-based elastomeric material.

Figure 4:
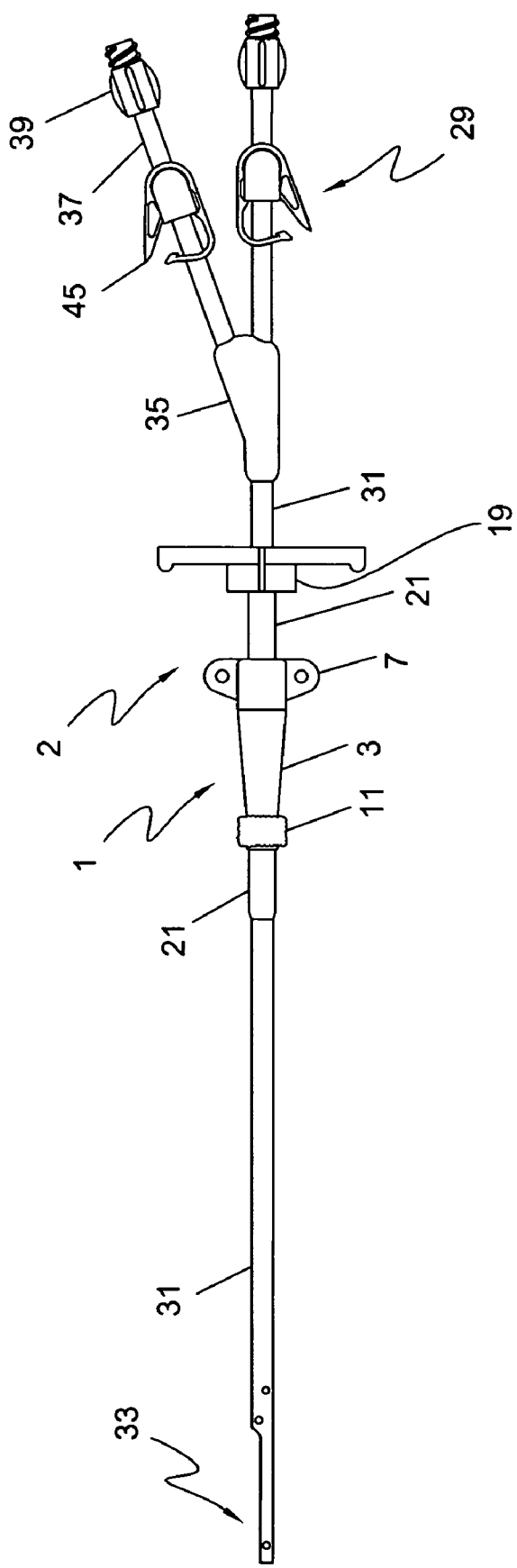
FIG. 4 is a plan view of the cuff positioning device positioned on a catheter in accordance with the present invention.

In another embodiment of the invention, illustrated in FIG. 4, the catheter retention assembly 2 is illustrated mounted on the catheter shaft 31. Although a chronic dialysis catheter is shown in FIG. 4, the embodiment is applicable to all types and sizes of venous access catheters. The dialysis catheter has extension tubes 37 for connection to a dialysis machine, extension tube clamps 45, a bifurcated catheter hub 35, catheter hub connectors 39, and a catheter shaft 31 which extends to the distal end 33 of the venous access catheter 29.

The catheter retention assembly 2 may be pre-mounted on the catheter shaft 31 or may be placed on the venous access catheter 29 by the physician just prior to the catheter insertion procedure. To assemble the catheter retention assembly 2 onto the venous access catheter 29, the distal end of the catheter 33 is inserted through the carrier system hub 19 and advanced through the carrier system lumen 23 until the carrier system hub 19 is in a position near the catheter hub 35, as shown in FIG. 4.

The dimensions of the outer diameter of the catheter shaft 31 and the inner diameter of the carrier system shaft 21 allow the catheter retention assembly 2 to slidably and longitudinally move along the catheter shaft 31. The inner diameter of the carrier system shaft 21 may be approximately 0.207 inches to provide a dose fit between the distal ends of both components to facilitate insertion but still allow sufficient luminal area to freely accommodate the outer diameter of the venous access catheter 29, which may be approximately 0.205 inches. Longitudinal movement of the catheter retention assembly 2 is also facilitated by the material of the carrier system shaft 21. Polytetrafluoroethylene (PTFE) materials, for example Teflon®, provide sufficient radial strength, stiffness, and a low enough co-efficient of friction to ensure that the catheter retention assembly 2 will slide smoothly and freely over the catheter shaft 31.

Figure 5A:
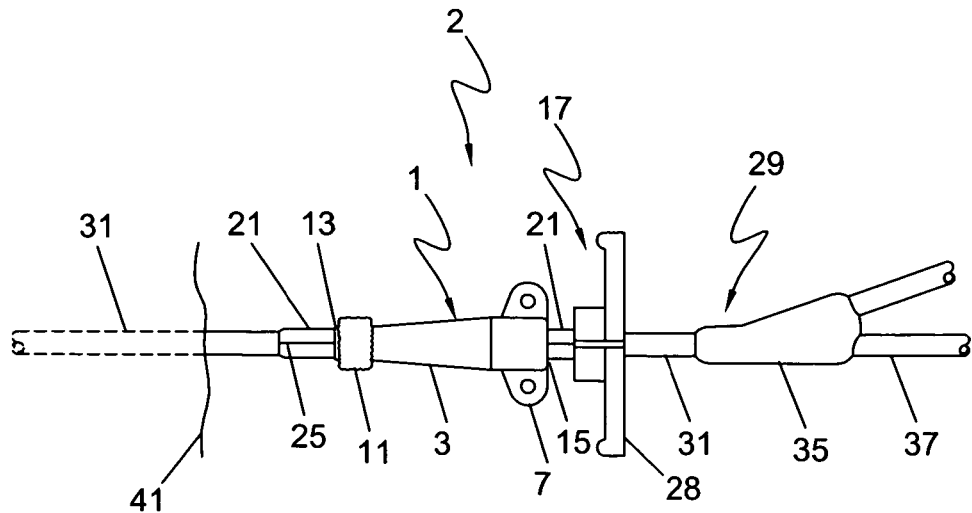
FIG. 5A is a partial view of the cuff positioning device positioned on a catheter during insertion into a skin incision site in accordance with the present invention.
Figure 5B:
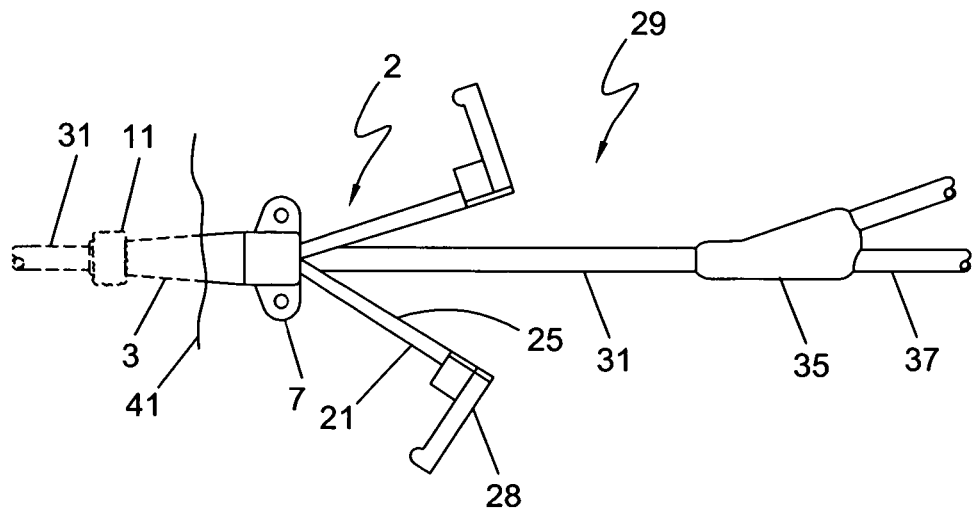
FIG. 5B is a partial view similar to that of FIG. 5A, except that the in-growth cuff has been partially positioned within the skin incision site, and the carrier system finger tabs have been separated to split the carrier system along a splittable line in accordance with the present invention.
Figure 5C:
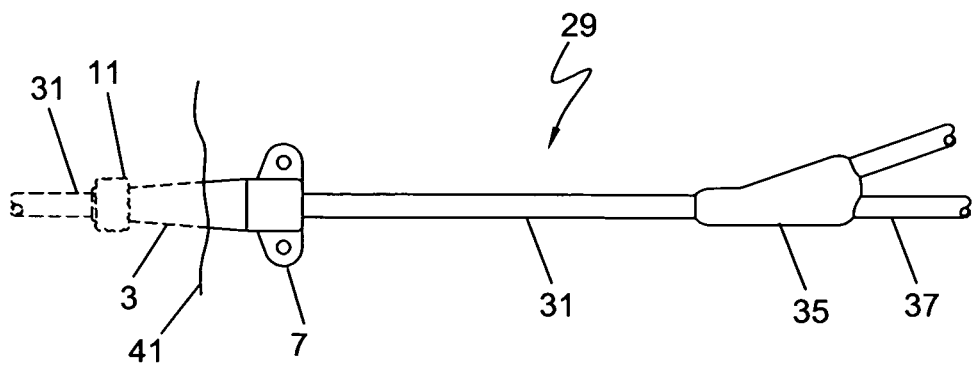
FIG. 5C is a partial view similar to that of FIG. 5B, after the carrier system has been removed in accordance with the present invention.

As illustrated in FIGS. 5A-5C, a method of optimally positioning and retaining the tip of a venous access catheter 29 relative to the in-growth cuff 11 at a desired location in a patient's body is provided. Typically, the tip of the venous access catheter 29 is placed in the right atrium 55 (ref. FIG. 1). The venous access catheter 29 may be optimally positioned and retained inside a patient's body by providing a catheter retention assembly 2. The catheter retention assembly 2 includes a cuff positioning device 1 with an in-growth cuff 11 mounted near the distal end 13 of the cuff positioning device 1. The venous access catheter 29 assembled with the catheter retention assembly 2 is placed in the patient's body by first inserting the venous access catheter 29 into a tunneled skin incision site 41 of a patient, positioning the distal end 33 (not shown) of the venous access catheter 29 at a desired location within the central venous system, moving the catheter retention assembly 2 to a desired location along the catheter shaft 31 by longitudinally sliding the catheter retention assembly 2 over the catheter shaft 31, and removing the carrier system 17 from the catheter retention assembly 2, so as to permanently fix the position of the cuff positioning device 1 and the catheter 29 relative to one another.

In FIG. 5A, after a skin incision site 41 is created in a patient's skin, the distal section of the catheter shaft 31 is inserted into the patient's vascular system (not shown) through a subcutaneous tunnel created below the patient's skin, as previously described. The remaining, or extracorporeal portion of the venous access catheter 29 is positioned outside of the skin incision site 41. The extracorporeal portion of the venous access catheter 29 includes a catheter retention assembly 2 in a longitudinally slidable arrangement with the catheter shaft 31. The catheter retention assembly 2 has a cuff positioning device 1 with a cuff positioning body 3 and an in-growth cuff 11 that is circumferentially located near the distal end 13 of the cuff positioning device 1. The cuff positioning device 1 also includes suture wings 7 that are disposed on each side of the cuff positioning body 3 at the proximal end 15 of the cuff positioning body 3.

In the pre-deployed state of the catheter retention assembly 2, the carrier system shaft 21 extends distally from the distal end 13 of the cuff positioning device 1 through the cuff positioning body 3 to the carrier system hub 19. At least two abutting carrier system finger tabs 28 are intersected by at least one longitudinal carrier system splittable line 25 along the longitudinal axis of the carrier system shaft 21 near the proximal end of the venous access catheter 29.

In FIG. 5B, the tip of the venous access catheter 29 (not shown) has been positioned at a desired location of therapeutic activity inside the patient's body. The cuff positioning body 3 with the in-growth cuff 11 mounted near the distal end 13 of the cuff positioning device 1 may be readily longitudinally advanced toward the distal end of the catheter shaft 31 and into the tunnel track through the skin incision site 41. The cuff positioning body 3 may be readily longitudinally moved in relation to the venous access catheter 29 due to a relatively low adherence between the carrier system lumen 23 and the outer surface of the venous access catheter 29.

The catheter retention assembly 2 is moved to a desired location by advancing the catheter retention assembly 2 relative to the skin incision site 41 while holding the venous access catheter 29 stationary. Once the physician has placed the catheter retention assembly 2 in the desired position, the carrier system 17 is removed from the cuff positioning device lumen 5. Removal of the carrier system 17 is facilitated by manually gripping and pulling the carrier system finger tabs 28 away from the catheter shaft 31 in opposite directions along the carrier system splittable line 25 and retracting the carrier system 17. The carrier system 17 is thus concurrently separated into two evenly proportioned sections for removal.

FIG. 5C illustrates the cuff positioning device 1 after the carrier system 17 has been completely removed from the venous access catheter 29. The cuff positioning device 1 is optimally positioned with the tapered distal portion of the cuff positioning body 3 and the in-growth cuff 11 inserted into the tunnel track. The distal portion of the cuff positioning body 3 remains adjacent to the skin incision site 41 outside of the tunnel track. The extracorporeal portion of the cuff positioning device 1 includes suture wings 7, which are used for suturing to the patient's skin surface in a location which minimizes patient discomfort.

When the carrier system 17 is removed, the cuff positioning body 3 circumferentially locks down around the catheter shaft 31. Specifically, the removal of the carrier system shaft 21 from the cuff positioning body 3 causes the inner wall 6 of the cuff positioning device 1 to contract from a first radially expanded state to a second radial state that is smaller than the first radially expanded state. The elastomeric material of the cuff positioning device 1, which has a high elastic limit, imparts sufficient elastic recoil characteristics to allow the inner wall 6 of the cuff positioning device 1 to expand and contract without plastic deformation. As an example, the cuff positioning device lumen 5 is held at a first state where the diameter of the inner wall 6 of the cuff positioning device 1 is equal to or greater than the carrier system shaft 21 outer diameter of approximately 0.227 inches, while the carrier system 17 is in place within the cuff positioning device lumen 5. Once the carrier system 17 is removed, the cuff positioning device inner wall 6 will return to its original diameter of approximately 0.200 inches. Thus, the cuff positioning device 1 is resilient allowing the inner wall 6 to return from a first expanded state, maintained by the radially outward force of the carrier system 17, to a second, contracted state in the absence of the radially outward-expanding force.

The second, contracted state of the inner wall 6 of the cuff positioning device 1 creates sufficient surface adherence between the cuff positioning device 1 and the catheter shaft 31, so as to permanently fix the cuff positioning device 1 at the desired location on the catheter shaft 31. Sufficient surface adherence is due to choosing a combination of materials with an appropriate co-efficient of friction, compression interference, or polymer cross-linking properties, such that the cuff positioning device 1 and the catheter shaft 31 are fixed in relation to one another. Once the carrier system 17 is removed, the cuff positioning device 1 cannot be moved from its longitudinal position on the catheter shaft 31. Thus, the surface adherence created between the inner wall 6 of the cuff positioning device 1 and the catheter shaft 31 allows for long term placement and retention of the cuff positioning device 1 and the venous access catheter 29 in relation to each other. This long term retention may be enhanced by additional friction or long term molecular migration between the cuff positioning device 1 and the catheter shaft 31. In addition, the surface adherence fit between the cuff positioning device inner wall 6 and the outer surface of the venous access catheter 29 is advantageous because it does not substantially compromise the luminal area of the catheter shaft 31.

Once the cuff positioning device 1 is positioned within the skin incision site 41 as desired, and the carrier system 17 is removed, the venous access catheter 29 may then be sutured in the preferred location on the patient's skin just adjacent to the skin incision site 41 using the suture wings 7. The suture wings 7 of the cuff positioning device 1 are optimally located in order to minimize patient discomfort, while simultaneously ensuring that the implanted catheter position remains fixed during the time period required for the in-growth cuff 11 to completely be incorporated into the subcutaneous tissue.

Figure 6A:
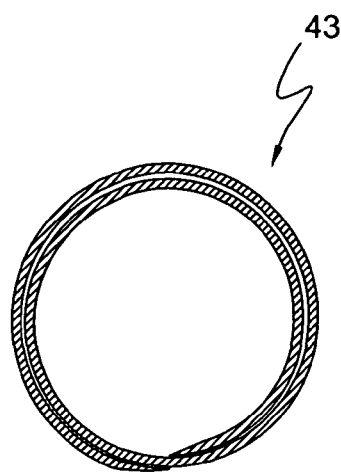
FIGS. 6A and 6B illustrate the use of a coiled spring to provide additional compressing force in accordance with the present invention.
Figure 6B:
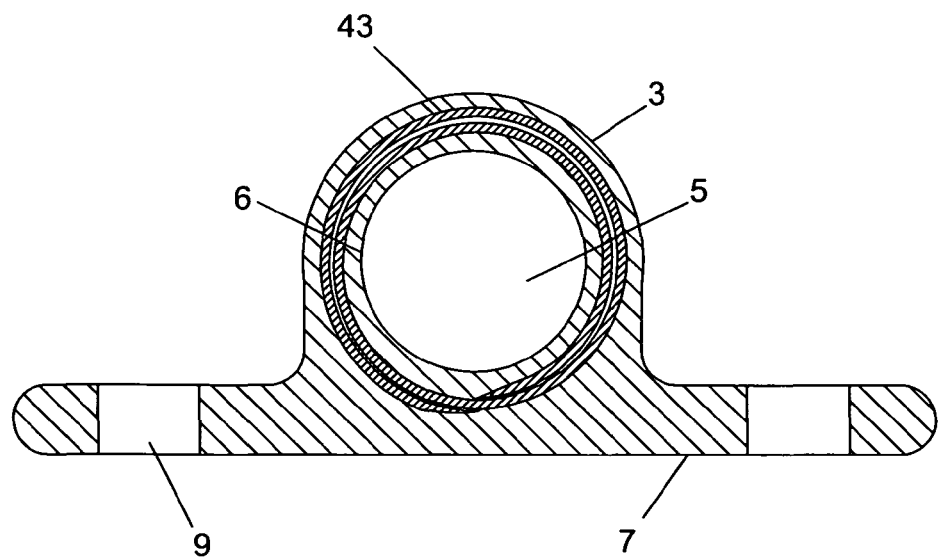

In another embodiment of the invention, as illustrated in FIGS. 6A and 6B, the invention further encompasses applying an additional radial compressive force to the inner wall 6 of the cuff positioning device 1 to enhance the radial contraction of the cuff positioning device lumen 5 after positioning the venous access catheter 29. The additional radial compressive force enhances the sufficient surface adherence between the inner wall 6 of the cuff positioning device 1 and the venous access catheter 29. The radial compressive force is applied by deploying a spring 43 that is embedded inside of the wall of the cuff positioning body 3. The spring 43 is illustrated in FIG. 6A. The spring 43 is designed to provide an enhanced compression force around the catheter shaft 31 after the carrier system 17 is removed. In effect, the spring 43 snaps the cuff positioning device 1 into place onto the venous access catheter 29.

As illustrated in FIG. 6B, the spring 43 is embedded inside the wall of the cuff positioning device 1 to provide additional compressive force. The spring 43 may embedded inside of the cuff positioning body 3 using standard molding techniques. Another method involves forming a circumferential groove in the cuff positioning device 1. The spring 43 is placed within the groove, and a secondary polymer layer is then added to the cuff positioning device 1 to fully encapsulate the spring 43. The spring 43 surrounds the cuff positioning device lumen 5. The spring 43 may be configured as a helical coil, C-clamp or other configuration. The spring 43 may be composed of any material that has shape memory characteristics. Preferably, the spring 43 may be made of any material including, but not limited to, stainless steel and nitinol. Most preferably, the spring 43 is composed of nitinol. The nitinol may be approximately 0.0085 inches in thickness. The internal diameter of the nitinol spring may be approximately 0.196 inches.

In yet another embodiment of the invention, as illustrated in FIGS. 7A through 7D, the cuff positioning device 1 allows a physician to exchange the venous access catheter 29 for a new catheter. Catheter exchanges are often done to address complications such as infection, catheter occlusion, or catheter mis-positioning. Catheter exchanges typically require creation of a new tunnel track through the subcutaneous tissue. A new cuff is placed as part of the exchange procedure. As result, temporary retention mechanisms must be used to fix the replacement catheter in place until in-growth of tissue into the new cuff has occurred, typically taking several weeks.

In the method of this invention, the same tunnel track may be used for the catheter exchange, thereby eliminating a time-consuming procedural step, as well as the discomfort and complications associated with creating a new tunnel track. The method of this invention is also advantageous in that the cuff positioning device 1 is not removed, thereby eliminating the need for temporary suturing or retention required if a new cuff was placed.

The method of exchanging the venous access catheter 29 involves coaxially mounting an expander 47 over the catheter shaft 33 and advancing it toward the distal end of the catheter 33. The expander 47 has an expander sheath 49 that may be tapered at the distal end 51 in order to facilitate entry of the distal end of the expander 51 between the cuff positioning device 1 and the catheter shaft 31. The expander sheath 49 may be a hollow tube that is made of any suitable material that is rigid and is capable of acting as a lumen expander. The expander sheath 49 may be comprised of one or more semi-cylindrical tubular structures. Preferably, the expander is a cannula made of stainless steel. FIG. 7A illustrates an expander sheath 49 after it has been mounted over the catheter shaft 31 of an indwelling catheter with a cuff positioning device 1.

The expander sheath 49 is then advanced between the inner wall 6 of the cuff positioning device lumen 5 and the outer wall of the venous access catheter 29, as illustrated in FIG. 7B, thereby expanding the lumen 5 of the cuff positioning device 1, removing the venous access catheter 29 from the cuff positioning device 1, placing a new catheter through the expander, and removing the expander. The expander sheath 49 is advanced between the inner wall 6 of the cuff positioning device lumen 5 and the outer wall of the venous access catheter 29 until the tapered distal end 51 of the expander 47 extends distally of the in-grown cuff 11. The radially expanding force of the expander sheath 49 causes the inner wall 6 of the cuff positioning device 1 to move from a first radially contracted state to a second radially expanded state. The elastic characteristics of the cuff positioning device 1 facilitate the lumen expansion.

Figure 7C:
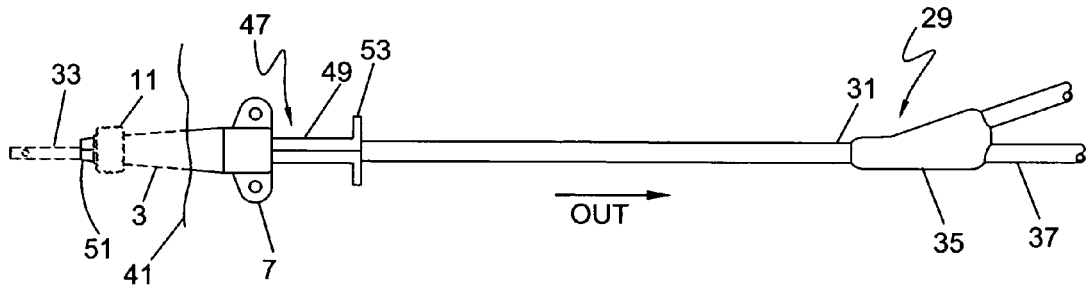
FIG. 7C is a partial view of a catheter with the expander sheath as the catheter is partially removed from the lumen of the cuff positioning device.

The venous access catheter 29 is then removed from the patient's body through the cuff positioning device lumen 5, as illustrated in FIG. 7C, by longitudinally retracting the catheter shaft 31 through the cuff positioning device lumen 5 in the direction indicated by the arrow. The catheter shaft 31 moves freely through the cuff positioning device lumen 5 because the radially outward force of the expander sheath 49 against the inner wall 6 of the cuff positioning device 1 creates an expanded cross-luminal area larger than the catheter shaft 31 outer diameter. The cuff positioning device 1 remains in a fixed position during the catheter removal due to retention by the in-growth cuff 11.

Figure 7D:
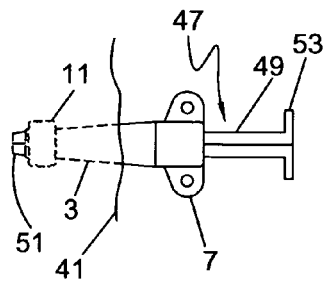
FIG. 7D is a partial view of the cuff positioning device and expander sheath after the catheter has been removed.

FIG. 7D illustrates the cuff positioning device 1 with the expander sheath 49 after the catheter has been completely removed from the patient. To place a new exchange catheter (not shown) within the same tunnel track, the physician inserts the distal tip of the new catheter into the lumen of the expander sheath 49 and advances it through the tunnel track. Advancement may be facilitated by using medical accessory devices well known in the art such as guidewires, tunnelers, dilators, and others. The new catheter advances freely through the cuff positioning device 1 due to the temporarily expanded lumen created by the expander sheath 49. After the catheter tip has been positioned in the desired location, the physician removes the expander sheath 49 from the cuff positioning device 1. Removal of the expander sheath 49 causes the inner wall 6 of the cuff positioning device 1 to move from its expanded state to a contracted state, thus creating an interference fit between the outer surface of the catheter shaft 31 and the inner wall 6 of the cuff positioning device 1. The interference fit ensures that the new catheter remains fixed in the desired state in relation to the cuff positioning device.

The catheter retention assembly 2 of the instant invention reduces the risk of infection and thereby enhances the antimicrobial properties of the venous access catheter 29 by providing for the optimal, secure positioning and retention of the venous access catheter 29 tip and the in-growth cuff 11 of the cuff positioning device 1 relative to each other inside a patient's body. The catheter retention assembly 2 also eliminates the time-consuming step of trimming or adjusting the venous access catheter 29 and decreases the chance of error in achieving the proper length of the venous access catheter 29.

This ability to simultaneously position the tip of the venous access catheter 29 and the in-growth cuff 11 on the cuff positioning device 1 allows the position of the venous access catheter 29 tip and the in-growth cuff 11 to be optimally placed and retained relative to each other and also allows for a tight, secure connection between the cuff positioning device 1 and the venous access catheter 29 so as to prevent fluid from leaking out of the venous access catheter 29 or the skin incision site 41.

The catheter retention assembly 2 and methods of insertion and removal also eliminate the problems associated with tunneling catheters too deeply because the catheter retention assembly 2 facilitates placement of the in-growth cuff 11 in an optimal position within a tunneling track. Placing the in-growth cuff 11 too deeply in the tunnel track may result in poor tissue incorporation into the in-growth cuff 11. Incomplete in-growth has been known to cause peri-catheter leakage, increased infection rates, and difficulty in removing the catheter. The catheter retention assembly 2 of the present invention also does not compromise or weaken the integrity of the venous access catheter 29. The catheter retention assembly 2 of the present invention also allows the venous access catheter 29 to be exchanged with a new catheter.

The foregoing proposed catheter could be applied to all types of venous access catheters, including, but not limited to, hemodialysis catheters, peritoneal catheters, PICC lines, central venous catheters, or tunneled venous access catheters. Most preferably, the cuff positioning device 1 is used with a tunneled venous access catheter. The preferred embodiment is exemplary of catheter positioning assemblies for use with catheters generally, and the detailed dimensions are given for example only. Such other structures are within the scope of the invention as claimed.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein, which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A catheter retention assembly for use with a catheter having an outer surface, wherein the catheter retention assembly comprises:
 a cuff positioning device having a distal end configured for insertion into a patient's body and an opposed proximal end configured to remain outside of a patient's body, the cuff positioning device comprising:
  a cuff positioning device wall having an outer wall surface and an inner wall surface defining a lumen extending between the distal end and proximal end that is configured to receive at least a portion of the catheter therein, wherein the cuff positioning device wall has a first constant wall thickness at the proximal end, a second, constant smaller wall thickness at the distal end, and an intermediate wall thickness between the proximal end and the distal end, wherein the intermediate wall thickness continuously decreases from the proximal end to the distal end, an in-growth cuff coaxially mounted at the distal end, and a clamp configured to exert a compressive force on at least a portion of the inner wall surface of the lumen, wherein at least a portion of the lumen of the cuff positioning device is selectively biasable between a first expanded radial state and a second radial state, and wherein the second radial state has an operative diameter that is less than the first expanded radial state and is less than the diameter of the outer surface of the catheter; and a unitary carrier system configured to be selectively received therein the lumen of the cuff positioning device in its first expanded radial state, wherein a portion of the carrier system extends distally of the cuff positioning device, wherein the carrier system is configured for selectively positioning the cuff positioning device axially relative to the outer surface of the catheter, and wherein, when the carrier system is removed, at least a portion of the cuff positioning device biases to the second radial state and compressively and coaxially contacts the outer surface of the catheter to selectively fix the position of the cuff positioning device relative to the catheter.

2. The catheter retention assembly of claim 1, wherein the clamp is at least partially embedded therein the wall of the cuff positioning device.

3. The catheter retention assembly of claim 1, wherein, when the carrier system is positioned therein the lumen of the cuff positioning device, the carrier system maintains substantially the elongate length of the lumen in the first expanded radial state.

4. The catheter retention assembly of claim 3, wherein removal of the carrier system causes the portion of the lumen of the cuff positioning device adjacent the clamp to contract to the second radial state due to the compressive force of the clamp acting thereon the inner wall surface of the lumen.

5. The catheter retention assembly of claim 1, comprising means for securing the cuff positioning device to a patient's skin.

6. The catheter retention assembly of claim 5, wherein the means for securing the cuff positioning device to a patient's skin comprises at least one suture wing disposed proximate the proximal end of the cuff positioning device.

7. The catheter retention assembly of claim 1, wherein the carrier system is composed of polytetrafluoroethylene.

8. The catheter retention assembly of claim 1, wherein the cuff positioning device comprises a resilient material.

9. The catheter retention assembly of claim 1, wherein the cuff positioning device comprises an elastomeric material that permits radial expansion and contraction of the lumen.

10. The catheter retention assembly of claim 1, wherein the outer surface of the cuff positioning device has a first diameter at the proximal end and a second, smaller, diameter at the distal end, and wherein at least a portion of the cuff positioning device tapers from the first diameter to the second diameter.

11. The catheter retention assembly of claim 1, wherein the carrier system comprises a pair of semi-cylindrical structures that cooperate to form a cylindrical carrier system body when positioned therein the cuff positioning device.

12. The catheter retention assembly of claim 1, wherein the carrier system comprises a substantially cylindrical carrier system body that comprises at least one splittable line that runs longitudinally along a portion of the carrier system body to permit manual longitudinal splitting and removal of the carrier system.

13. A catheter retention assembly comprising:
a catheter having an outer surface;
a bifurcated catheter hub coupled to the catheter;
a cuff positioning device having a distal end configured for insertion into a patient's body and an opposed proximal end configured to remain outside of a patient's body, the cuff positioning device comprising:

a cuff positioning device wall having an outer wall surface and an inner wall surface defining a lumen extending between the distal end and proximal end that is configured to receive at least a portion of the catheter therein, wherein the cuff positioning device wall has a first constant wall thickness at the proximal end, a second, constant smaller wall thickness at the distal end, and an intermediate wall thickness between the proximal end and the distal end, wherein the intermediate wall thickness continuously decreases from the proximal end to the distal end, an in-growth cuff mounted at the distal end, and a clamp configured to exert a compressive force on at least a portion of the inner wall surface of the lumen, wherein at least a portion of the lumen of the cuff positioning device is selectively biasable between a first expanded radial state and a second radial state, wherein the second radial state has an operative diameter that is less than the first expanded radial state and is less than the diameter of an outer surface of the catheter, and wherein the cuff positioning device is positioned on the catheter therebetween the bifurcated catheter hub and a distal end of the catheter; and a unitary carrier system configured to be selectively received therein the lumen of the cuff positioning device in its first expanded radial state, wherein a portion of the carrier system extends distally of the cuff positioning device, wherein the carrier system is configured for selectively positioning the cuff positioning device axially relative to the outer surface of the catheter, and wherein, when the carrier system is removed, at least a portion of the cuff positioning device biases to the second radial state and compressively and coaxially contacts the outer surface of the catheter to selectively fix the position of the cuff positioning device relative to the catheter.

14. The catheter retention assembly of claim 13, wherein the carrier system comprises a pair of semi-cylindrical structures that cooperate to form a cylindrical carrier system body when positioned therein the cuff positioning device.

15. The catheter retention assembly of claim 13, wherein the carrier system comprises a substantially cylindrical carrier system body that comprises at least one splittable line that runs longitudinally along a portion of the carrier system body to permit manual longitudinal splitting and removal of the carrier system.

16. The catheter retention assembly of claim 13, wherein, when the carrier system is positioned therein the lumen of the cuff positioning device, the carrier system maintains substantially the elongate length of the lumen in the first expanded radial state.

17. The catheter retention assembly of claim 16, wherein removal of the carrier system causes the portion of the lumen of the cuff positioning device adjacent the clamp to contract to the second radial state due to the compressive force of the spring acting thereon the inner wall surface of the lumen.

18. The catheter retention assembly of claim 13, comprising means for securing the cuff positioning device to a patient's skin.

* * * * *